United States Patent
Troili et al.

(10) Patent No.: US 10,617,841 B2
(45) Date of Patent: Apr. 14, 2020

(54) VAPORIZER ARRANGEMENT FOR A BREATHING APPARATUS

(75) Inventors: Carl-Erik Troili, Danderyd (SE); Mario Loncar, Ekero (SE); Ake Larsson, Jarfalla (SE)

(73) Assignee: Maquet Critical Care AB, Solna (SE)

(*) Notice: Subject to any disclaimer, the term of this patent is extended or adjusted under 35 U.S.C. 154(b) by 1690 days.

(21) Appl. No.: 14/369,081

(22) PCT Filed: Dec. 28, 2011

(86) PCT No.: PCT/SE2011/051597
§ 371 (c)(1),
(2), (4) Date: Oct. 22, 2014

(87) PCT Pub. No.: WO2013/100830
PCT Pub. Date: Jul. 4, 2013

(65) Prior Publication Data
US 2015/0040900 A1 Feb. 12, 2015

(51) Int. Cl.
*A61M 16/18* (2006.01)
*A61M 16/16* (2006.01)
(Continued)

(52) U.S. Cl.
CPC .......... *A61M 16/18* (2013.01); *A61M 16/024* (2017.08); *A61M 16/104* (2013.01);
(Continued)

(58) Field of Classification Search
CPC .............. A61M 16/18; A61M 16/0003; A61M 16/1015; A61M 16/109; A61M 16/202;
(Continued)

(56) References Cited

U.S. PATENT DOCUMENTS 3,515,155 A * 6/1970 Haffner ................. A61M 16/12
137/207
3,593,735 A * 7/1971 Reiher ..................... A62B 7/14
128/204.22
(Continued)

FOREIGN PATENT DOCUMENTS

DE 41 05 971 8/1992
EP 0 722 748 7/1996
(Continued)

*Primary Examiner* — Kendra D Carter
*Assistant Examiner* — Elliot S Ruddie
(74) *Attorney, Agent, or Firm* — Schiff Hardin LLP

(57) ABSTRACT

A vaporizer arrangement for a breathing apparatus serves the double purpose of vaporizer and pressurized supply of vapor-containing gas for direct delivery to a patient. The vaporizer arrangement has at least a first gas inlet channel for conveying a flow of a carrier gas into a vaporization chamber, a vaporizer for vaporizing a liquid into the carrier gas in the vaporization chamber, and a gas outlet channel for conveying a flow of vapor-containing carrier gas out of the vaporization chamber and toward the patient. The vaporizer arrangement further has a gas flow regulator that maintains the carrier gas within the vaporization chamber at an overpressure, and that controls the flow of vapor-containing carrier gas out of the vaporization chamber in a variable manner.

15 Claims, 5 Drawing Sheets

Figure 1:
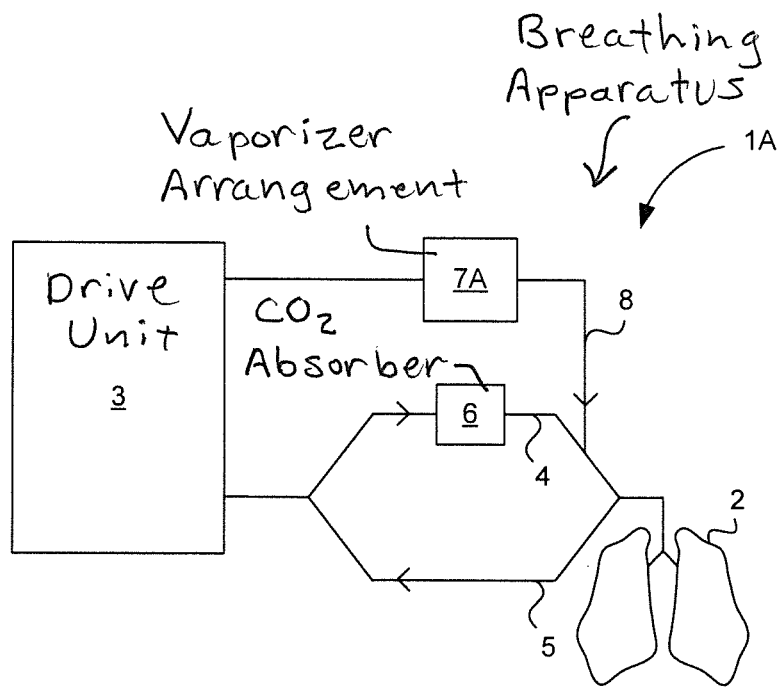

(51) Int. Cl.
*A61M 16/10* (2006.01)
*A61M 16/12* (2006.01)
*A61M 16/00* (2006.01)
*A62B 7/02* (2006.01)
*A61B 5/091* (2006.01)

(52) U.S. Cl.
CPC ...... *A61M 16/109* (2014.02); *A61M 16/1015* (2014.02); *A61M 16/12* (2013.01); *A61M 16/16* (2013.01); *A62B 7/02* (2013.01); *A61B 5/091* (2013.01); *A61M 2016/0027* (2013.01); *A61M 2016/0039* (2013.01); *A61M 2016/102* (2013.01); *A61M 2202/0208* (2013.01); *A61M 2202/0283* (2013.01); *A61M 2205/3331* (2013.01); *A61M 2205/3653* (2013.01)

(58) Field of Classification Search
CPC ............ A61M 16/024; A61M 16/0051; A61M 16/104; A61M 16/12; A61M 16/16; A61M 2016/0027; A61M 2016/0039; A61M 2016/102; A61M 2202/0007; A61M 2202/0208; A61M 16/183; A62B 7/02; A62B 7/04; A61B 5/091
USPC ............ 128/203.12, 203.13, 203.14, 203.15, 128/203.25, 204.21, 204.22; 137/88
See application file for complete search history.

(56) References Cited

U.S. PATENT DOCUMENTS

| | | | | |
|---|---|---|---|---|
| 4,023,587 | A * | 5/1977 | Dobritz | A61M 16/12 128/203.25 |
| 5,299,568 | A * | 4/1994 | Forare | A61M 16/12 128/205.11 |
| 5,383,449 | A | 1/1995 | Forare et al. | |
| 7,438,072 | B2 | 10/2008 | Izuchukwu | |
| 2009/0205661 | A1* | 8/2009 | Stephenson | A61M 16/0051 128/204.21 |
| 2011/0023879 | A1* | 2/2011 | Vandine | A61M 16/0051 128/204.21 |
| 2011/0132364 | A1 | 6/2011 | Ogilvie et al. | |

FOREIGN PATENT DOCUMENTS

| | | |
|---|---|---|
| EP | 0 958 842 | 11/1999 |
| EP | 1 402 916 | 3/2004 |
| EP | 2 489 392 | 8/2012 |
| JP | 11076779 | 3/1999 |

* cited by examiner ing apparatus, as well we a breathing apparatus
VAPORIZER ARRANGEMENT FOR A BREATHING APPARATUS

BACKGROUND OF THE INVENTION

Field of the Invention

The present invention concerns a vaporizer arrangement for breathing apparatus, as well we a breathing apparatus embodying such a vaporizer arrangement, as well as a gas tank arrangement for a breathing apparatus.

Description of the Prior Art

In breathing apparatuses vaporized liquid, such as vaporized anaesthetic or vaporized water, is often added to the breathing gas before the breathing gas is delivered to the patient. Normally, a flow of gas is directed through a vaporization chamber in which it absorbs the vaporized liquid before being delivered to the patient, either directly or after subsequent mixing with additional gas components.

For example, in certain types of anaesthesia apparatuses, a flow of fresh gas is directed through a vaporization chamber of an anaesthetic vaporizer, in which it absorbs vaporized anaesthetic liquid. Examples of anaesthetic vaporizers are disclosed in e.g. EP 0958842 and EP1402916 (A1). These documents disclose injection vaporizers wherein fine droplets of volatile anaesthetic liquid is injected into a flow of breathing gas passing through the vaporization chamber. Another type of anaesthetic vaporizer is the so called flow-by vaporizer wherein the flow of breathing gas simply passes over a surface of liquid anaesthetic within the vaporization chamber.

This flow-by principle is often used also in water vaporizers, often referred to as humidifiers. Humidifiers are often used in ventilators in order to humidify breathing gas before the breathing gas is delivered to the patient undergoing the ventilatory treatment. Humidifying the breathing gas is desirable since the gas delivered by the ventilator is dry, which may cause the patient to be dried out and cooled down. In flow-by humidifiers, a flow of gas is conveyed through a vaporization chamber in which it passes over or through heated water in order to absorb water vapor before being delivered to the patient. Normally, in both anaesthesia apparatuses and ventilators, the gas that is directed through the vaporizer chamber in order to absorb the vaporized liquid, hereinafter referred to as the carrier gas, passes freely through the vaporization chamber and onto the patient or a subsequent mixing stage where the vapor-containing gas is mixed with other gas components before delivery to the patient.

One problem associated with this "free flow technique" is that the carrier gas is unable to absorb a sufficient amount of vaporized liquid on its way through the vaporization chamber and hence that the humidity of the breathing gas, or the concentration of anaesthetic agent in the breathing gas, is too low when delivered to the patient. This is particularly relevant for high flows of carrier gas.

Another problem is that the concentration of vapor-content in the gas flow from the vaporizer varies substantially if the gas flow through the vaporizer varies. This is because low flows give the gas more time to absorb the vapor within the chamber than high flows, and also because high flows decreases the rate of vaporization in the vaporization chamber as they cool down the often heated vaporization chamber. This fact makes it hard to deliver varying flows of vapor-containing gas with constant vapor-content to the patient.

In some applications where low flows of carrier gas are used, the problem is the opposite, namely that the vapor concentration becomes too high if the entire flow of carrier gas is directed through the vaporization chamber. Therefore, there are vaporizers according to prior art wherein the flow of carrier gas is divided into two separate flows upstream of the vaporization chamber; one which is directed through the vaporization and one that bypasses the vaporization chamber. The two separate flows are then mixed again, downstream of the vaporization chamber. Here too, it is very hard to maintain a stable vapor concentration in the carrier gas, especially if the flow of carrier gas through the vaporization chamber varies over time.

Yet another problem which mainly relates to flow-by vaporizers (and not injection vaporizers) is that the vapor content in the relatively small vaporization chamber is quickly absorbed by the flow of carrier gas, which also makes the vapor concentration in the vapor-containing gas vary in time. This effect is further enhanced by the fact that the flow of carrier gas passing over or through the liquid in the vaporization chamber cools the liquid, which reduces the rate of vaporization.

A slightly different problem related to breathing apparatuses equipped with vaporizer arrangements is the complexity of the gas flow circuit. In both anaesthesia apparatuses and ventilators there is often a desire to use a carrier gas in form of a well-defined gas mixture comprising two or more gas components, such as a mixture of air, oxygen, and/or nitrous oxide. Therefore, the carrier gas is often a gas mixture formed in a gas mixing chamber disposed upstream of the vaporization chamber and connected in series therewith. An example of a gas mixing chamber suitable for this purpose is the receiver tank 12 of FIG. 1 in U.S. Pat. No. 5,383,449. There is a desire to reduce the complexity and hence the cost of this type of gas flow circuits where there is a need for vaporization of liquid into a multi-component gas mixture.

SUMMARY OF THE INVENTION

It is an object of the present invention to provide a vaporizer arrangement that solves or at least mitigates one or more of the above mentioned problems. In particular, it is an object of the invention to provide a vaporizer arrangement that is capable of delivering varying flows of vapor-containing gas with a substantially stable vapor concentration.

This object is achieved by a vaporizer arrangement for a breathing apparatus, comprising:
- at least a first gas inlet channel that conveys a flow of a carrier gas into a vaporization chamber;
- a vaporizer that vaporizes a liquid into the carrier gas in the vaporization chamber, and
- a gas outlet channel that conveys a flow of vapor-containing carrier gas out of the vaporization chamber and towards a patient.

The vaporizer arrangement further has gas flow regulating means operable to maintain the carrier gas within the vaporization chamber at an overpressure, and to control the flow of vapor-containing carrier gas out of the vaporization chamber in a variable manner.

To this end, the gas flow regulating means may comprise a controllable valve arranged in the gas outlet channel.

That the gas flow regulating means is capable of maintaining the carrier gas in the vaporization chamber means that the gas flow regulating means is configured to temporally interrupt the flow of vapor-containing carrier gas out of the vaporization chamber or at least temporally make the flow of vapor-containing carrier gas out of the vaporization chamber less than the flow of carrier gas into the vaporization chamber.

An effect of maintaining the carrier gas in the vaporization chamber is that the concentration of the vaporized liquid in the carrier gas can be increased compared to prior art solutions in which the carrier gas passes freely through the vaporization chamber. This is because the carrier gas has more time to absorb the vaporized liquid. This is particularly useful in high-flow applications where high flows of vapor-containing gas are to be delivered to the patient.

That the carrier gas is maintained in the vaporization chamber further has the effect of mitigating undesired variations in concentration of the vapor component in the vapor-containing carrier gas leaving the vaporization chamber. This is because the carrier gas/vapor mixture will have more time to form a homogeneous gas mixture within the vaporization chamber.

That the carrier gas is maintained at an overpressure means that the pressure in the vaporization chamber is higher than the pressure in the gas outlet channel.

The effect of maintaining the carrier gas at an overpressure is that the carrier gas that is maintained in the vaporization chamber can be delivered to the patient under influence of the elevated pressure in the vaporization chamber. This means that no external flow generating means has to be used to supply the vapor-containing carrier gas from the vaporization chamber to the patient. Another effect is that the vaporization chamber is capable of storing a larger volume of vapor-containing gas at the elevated pressure, for subsequent delivery to the patient.

Maintaining the carrier gas at an overpressure in the vaporization chamber further has the effect that a large volume of vapor-containing gas can be "prefabricated" for subsequent delivery to the patient. This is particularly useful in low flow applications where low flows of vapor-containing gas are to be delivered to the patient. For example, in ventilation of neonatal patients having a tidal volume of just a few milliliters it is difficult to deliver a low flow of vapor-containing carrier gas having a substantially constant vapor-component concentration using free-flow vaporizers according to prior art. Especially when using injection vaporizers having a certain minimum injection volume of liquid. In free-flow vaporizers according to prior art it may also be difficult to monitor the vapor-component concentration in low flows of vapor-containing gas since the amount of the vapor-component in the small volume of gas available for measurement put high demands on the sensitivity of the gas analyzers and introduces a high degree of uncertainty in gas composition measurements. By maintaining a large volume of carrier gas (several times the tidal volume of neonatal patients) in the vaporization chamber, a low flow of prefabricated and homogeneously mixed vapor-containing gas can be delivered from the vaporization chamber under the control of the gas flow regulating means. Furthermore, gas composition determination can be carried out on the large volume of gas in the vaporization chamber, which increases the accuracy in the determination of the vapor-component concentration in the gas that is to be delivered to the patient.

Thus, at least to some extent, the proposed vaporizer arrangement forms a new type of vaporizer arrangement having a combined vaporization chamber and pressurized storage tank for vapor-containing gas.

Due to the above mentioned advantages following the maintenance of the carrier gas in the vaporization chamber at an overpressure, the vaporizer arrangement is capable of delivering a varying flow of gas having a much more stable concentration of the vapor component than vaporizer arrangements according to prior art.

The capability of delivering a varying flow of vapor-containing gas with a stable vapor concentration is advantageous in that said flow can be varied based on patient-related and/or application-related parameters while still delivering a well-defined dose of the vapor-component to the patient. For example, the flow regulating means may be configured to vary the flow of vapor-containing gas out of the vaporization chamber based on any of, or any combination of:

pressure and/or flow measurements obtained downstream of the vaporization chamber,
gas composition measurements obtained in and/or downstream of the vaporization chamber,
a preset tidal volume,
a preset patient pressure, and
a preset fresh gas flow.

Preferably, the flow regulating means is operable to control also the flow of carrier gas into the vaporization chamber. To this end, the gas flow regulating means may comprise a controllable valve arranged in the gas inlet channel. Active control of the flow of carrier gas into the vaporization chamber is not a necessity if the carrier gas is delivered to the gas inlet channel at a suitable overpressure. However, it is advantageous since vapor-containing carrier gas otherwise might have to be released through a flush valve or the like in order to avoid pressure build-up in the vaporization chamber, which pressure build-up otherwise would cause too high flows of vapor-containing gas to the patient.

The flow of carrier gas into the vaporization chamber is preferably controlled based on measurements indicative of the pressure within the vaporization chamber. Such measurements may be obtained by measuring the pressure within the vaporization chamber, or by measuring the flows into and out of the vaporization chamber. In some applications it may also be advantageous to control the flow of carrier gas into the vaporization chamber based on the temperature within the vaporization chamber and/or the gas composition in or downstream of the vaporization chamber.

Thus, according to a preferred embodiment of the invention, the flow regulating means is operable to control both the flow of carrier gas into the vaporization chamber and the flow of vapor-containing carrier gas out of the vaporization chamber. Preferably, the outflow of vapor-containing gas is controlled based on the pressure and/or flow measurements obtained downstream the vaporization chamber, indicative of the respiratory phase of the patient, and the inflow of carrier gas is controlled based on a parameter that is indicative of the pressure within the vaporization chamber. This allows the flow of vapor-containing carrier gas from the vaporization chamber to be synchronized with the respiratory phases of the patient.

Preferably, the flow regulating means is configured to control said inflow and outflow such that during expiration of the patient, the outflow is either interrupted or decreased to a low bias flow, while the inflow is controlled such that a desired overpressure is obtained in the vaporization chamber. When the desired overpressure is obtained, the inflow of carrier gas is preferably interrupted. During inspiration of the patient, the outflow is increased and controlled such that a desired flow of vapor-containing carrier gas is delivered to the patient, whereby the pressure in the vaporization chamber decreases and the procedure starts over again. During inspiration of the patient, the flow of carrier gas into the vaporization chamber may be controlled to prevent the pressure in the vaporization chamber to fall too much. In other embodiments, however, flow of carrier gas into the vaporization chamber may be prevented during inspiration of the patient.

In some embodiments, the gas flow regulating means may be operable to fully interrupt the flow of vapor-containing gas out of the vaporization chamber, at least during expiration phases of the patient. This type of "semi-closed vaporizer arrangement" is advantageous in that it can be ascertained that the carrier gas is maintained in the vaporization chamber at least for a minimum period of time before being delivered to the patient during inspiration. It is also advantageous in that it provides for fast pressure build-up within the vaporization chamber during interruption of the outflow, thereby allowing higher flows of vapor-containing gas to be delivered to the patient after the interruption. Another advantage with the semi-closed vaporizer arrangement is that the flow of vapor-containing gas from the vaporization chamber can be stopped if it is found that too high doses of the vapor-component is or has been delivered to the patient. Therefore, the gas flow regulating means is preferably also capable of interrupting the flow of vapor-containing gas out of the vaporization chamber during inspiration phases of the patient.

Preferably, the gas flow regulating means is configured to maintain the carrier gas in the vaporization chamber at an overpressure that never exceeds a maximum pressure threshold value.

That the overpressure never exceeds a maximum threshold value has the effect of avoiding too high flows of vapor-containing gas to the patient should the flow regulating means malfunction, e.g. should an outlet valve in the gas outlet channel get stuck in a fully open position. This is particularly important in ventilation of patients with reduced lung capacity (e.g. small patients) where high flows of breathing gas could damage the pulmonary system of the patient.

The gas flow regulating means is preferably configured to control the flow of gas into and out of the vaporization chamber such that the maximum pressure threshold value is obtained at the end of expiration of the patient (i.e. just before transition from an expiratory phase to an inspiratory phase of the patient). The maximum pressure threshold value can hence be seen as a target pressure for the pressure in the vaporization chamber at the end of expiration of the patient, i.e. as an end-expiratory target pressure.

Furthermore, the gas flow regulating means is preferably configured to maintain the gas in the vaporization chamber at an overpressure that always exceeds a certain minimum pressure threshold value. Typically, the pressure in the vaporization chamber reaches a minimum value at the end of inspiration of the patient (i.e. just before transition from an inspiratory phase to an expiratory phase). The pressure in the vaporization chamber at the end of an inspiration phase of the patient will hereinafter be referred to as the end-inspiratory pressure in the vaporization chamber. The gas flow regulating means may hence be configured to keep this end-inspiratory pressure above a minimum inspiratory pressure threshold value.

The effect of always maintaining the pressure in the vaporization chamber above a certain minimum value has the effect of always being able to deliver a certain minimum flow to the patient. This is important in order to deliver a sufficient dose of the vapor-component to the patient, and, in applications where the vaporizer arrangement is used to deliver the entire tidal volume to an adult patient with high lung capacity, to be capable of delivering the entire tidal volume during the time of an inspiration phase. The ability to deliver a certain minimum flow may also be important in situations where the patient flow must be maintained above a certain threshold value in order to keep the airways of the patient open.

In some embodiments, flow of carrier gas into the vaporization chamber is prevented during inspiration phases of the patient, and the end-expiratory target pressure is set high enough to ensure that the pressure in the vaporization chamber does not fall below the minimum pressure threshold value during the end of the inspiration phases.

In other embodiments, the end-expiratory target pressure may not be that high and flow of carrier gas into the vaporization chamber during inspiration phases may be permitted and controlled by the gas flow regulating means such that the pressure in the vaporization chamber is maintained above the minimum pressure threshold value throughout the entire inspiration phases.

Thus, the gas flow regulating means of the vaporizer arrangement according to the invention is preferably configured to control the flow of carrier gas into the vaporization chamber and the flow of vapor-containing carrier gas out of the vaporization chamber such that the overpressure in the vaporization chamber is always maintained between a minimum pressure threshold value and a maximum pressure threshold value.

These maximum and minimum pressure threshold values are preferably selected based on one or more design parameters, including but not limited to the tidal volume of the currently ventilated patient, the dynamics of an outlet valve arranged in the gas outlet channel for controlling the flow of vapor-containing carrier gas out of the vaporization chamber, and a desired minimum and/or maximum flow of vapor-containing gas out of the vaporization chamber.

Not only the overpressure at which the carrier gas is maintained in the vaporization chamber but also the volume of the vaporization chamber is a design parameter that should be adapted to the intended use of the vaporizer arrangement, and so to the above listed parameters. Yet another parameter that must be taken into account when it comes to the volume of the vaporization chamber is design requirements regarding the size of the vaporizer arrangement.

Preferably, the volume of the vaporization chamber should be between 500 ml and 4000 ml where the larger chamber is optimized for situations in which the carrier gas is delivered to the vaporization chamber at a pressure of approximately 0.5 bar and the smaller chamber is optimized for situations in which the carrier gas is delivered at a pressure approximately 4 bar. With an outlet valve being able to deliver a desired flow to the patient, preferably above 120 lpm within the pressure range of the chamber (i.e. between the minimum and maximum pressure threshold values), the chamber will be able to deliver a tidal volume of 1000 ml with no restrictions apart from the maximum flow limit set by the valve.

Typical gas flow valves suitable for use in this type of applications have operational ranges making them capable of maintaining a flow through the valve above a given threshold value as long as the pressure drop over the valve is no more than half the starting pressure. Therefore, the minimum pressure threshold value is preferably half the maximum pressure threshold value or more, and the outlet valve is preferably adapted to permit flows above 120 lpm within this pressure range. Furthermore, the volume of the vaporization chamber is preferably selected such that said desired flow (e.g. at least 120 lpm) can be delivered during a time period making the delivered volume of vapor-containing gas correspond to at least a tidal volume of an adult patient with normal lung capacity, i.e. a volume of at least 600 ml.

Even more preferably, the volume of the vaporization chamber is selected such that some gas will remain in the vaporization chamber even if the entire tidal volume of gas is delivered to an adult patient with normal lung capacity from the vaporization chamber during an inspiration phase. This has the effect that at least some carrier gas may be maintained in the vaporization chamber during at least one respiratory cycle (i.e. an inspiration phase and an expiration phase), thus providing for even higher and even more stable concentrations of vapor in the vapor-containing carrier gas delivered to the patient.

In a preferred embodiment of the invention making the vaporizer arrangement suitable for most situations, the volume of the vaporization chamber is at least 2000 ml and the flow regulating means is operable to obtain an end-expiratory pressure in the vaporization chamber of at least 1 bar, relative to the pressure in the gas outlet channel. A vaporization chamber volume of at least 2000 ml and a relative end-expiratory pressure of at least 1 bar ensure that the vaporizer arrangement is capable of delivering a flow of vapor-containing carrier gas of at least 120 l/min at half the end-expiratory pressure, i.e. at a relative pressure of 0.5 bar. This means that the vaporizer arrangement will be capable of delivering a volume of at least 1 liter of vapor-containing carrier gas to the patient, even during short inspiratory phases, with a flow that never falls below 120 l/min. In embodiments where the gas flow regulating means has a controllable outlet valve for controlling the flow of vapor-containing gas out of the vaporization chamber, the dynamics of the outlet valve should be adapted to allow flows of at least 120 lpm through the valve at an overpressure of 0.5 bar upstream the valve.

In another exemplary embodiment of the invention, the vaporization chamber has a volume of approximately 1000 ml, the end-expiratory target pressure in the vaporization chamber is approximately 2 bar, and the minimum pressure threshold value in the vaporization chamber is approximately 1 bar.

In yet another exemplary embodiment of the invention, the vaporization chamber has a volume of approximately 500 ml, the end-expiratory target pressure in the vaporization chamber is approximately 4 bar, and the minimum pressure threshold value in the vaporization chamber is approximately 2 bar.

Thus, in order to deliver sufficiently large tidal volumes of vapor-containing gas at sufficiently high flows, even at relatively low inlet pressures (i.e. when the carrier gas is delivered at relatively low pressures to the vaporization chamber), the volume of the vaporization chamber should be at least 500 ml, preferably at least 1000 ml, and even more preferably at least 2000 ml.

In all exemplary embodiments, the outlet valve of the vaporizer arrangement is preferably adapted to deliver a flow of at least 120 lpm within the pressure range defined by the end-expiratory target pressure (i.e. the maximum pressure threshold value) and the minimum pressure threshold value. It should be appreciated that all vaporization chamber pressures discussed above are pressures relative to the pressure in the gas outlet channel of the vaporizer arrangement. In embodiments where the gas flow regulating means has a controllable outlet valve to control the flow of vapor-containing gas out of the vaporization chamber, this corresponds to the pressure upstream the outlet valve relative to the pressure downstream the outlet valve. Normally, the absolute pressure in the gas flow circuit of a breathing apparatus (including the gas outlet channel) is approximately 1 atmosphere, or a few $cmH_2O$ above 1 atmosphere.

In cases where the vaporizer arrangement is used to deliver very small tidal volumes to the patient, it should be appreciated that the end-expiratory target pressure may be reduced substantially. If, for example, the maximum tidal volume of the patient is no more than 50 ml, the gas flow regulating means may be configured to maintain the carrier gas in the vaporization chamber at an overpressure that never exceeds 0.025 bar relative to the pressure in the gas outlet channel.

In some embodiments, a compressor may be used to deliver pressurized carrier gas to vaporization chamber. Such a compressor may be included in the vaporizer arrangement or the breathing apparatus of which the vaporizer arrangement forms a part. The compressor for the vaporization chamber shall be designed to deliver the minute volume desired by the breathing apparatus, and preferably more than 30 lpm. The above described preferred embodiment of the invention ensures that the vaporizer arrangement can be used to deliver the entire tidal volume of gas to the patient when used together with such a compressor, even when large tidal volumes have to be delivered to the patient at high flows.

In other embodiments, the carrier gas may be supplied to the vaporization chamber directly from a wall outlet delivering carrier gas at a pressure of approximately 4 bar. In embodiments where the gas inlet channel(s) of the vaporizer arrangement is connected directly to such a wall outlet, the end-expiratory target pressure in the vaporization chamber maybe set to approximately 4 bar, while the minimum pressure threshold value may be approximately 2 bar. In this case a vaporization chamber volume of 0.5 liter is sufficient in order to deliver more than one liter of vapor-containing gas to the patient with a flow that never falls below 120 lpm. It should further be noted that if the outflow from the vaporization chamber is controlled by means of a controllable outlet valve, the dynamics of said outlet valve also has impact on the vaporizer arrangement's capability of delivering high flows. To this end, the gas flow regulating means may be configured to control the overpressure in the vaporization chamber based on the dynamics of such an outlet valve.

As indicated above, the vaporizer arrangement may be adapted to deliver an entire tidal volume of vapor-containing gas to the patient. This opens up for new uses of the vaporizer arrangement. For example, as will be described below with reference to FIGS. 1 and 2, the vaporizer arrangement may be used in an anaesthesia apparatus to deliver a flow of fresh gas that is subsequently added to an inspiration branch of a circle system in which exhalation gases exhaled by the patient are resupplied to the patient after removal of carbon dioxide. The capability of the vaporizer arrangement to deliver an entire tidal volume to the patient and to synchronize the delivery of gas with the respiratory phases of the patient makes it possible to disconnect the circle system and to ventilate the patient only by means of the vaporizer arrangement.

The vaporizer arrangement is particularly intended to serve as an anaesthetic vaporizer for vaporization of anaesthetic liquid or as a humidifier for vaporization of water.

However, the vaporizer arrangement may also be used for vaporization of other liquids, such as other medical liquids having a therapeutic effect on a patient being connected to the breathing apparatus. It is also contemplated that the vaporizer arrangement may be used for simultaneous vaporization of more than one type of liquid into the carrier gas.

According to another aspect of the invention, the vaporizer arrangement has a first gas inlet channel and at least a second gas inlet channel for introducing a first and a second gas, respectively, into the vaporization chamber, so as to allow the first gas and second gas to mix within the vaporization chamber to form said carrier gas. The gas flow regulating means of the vaporizer arrangement may then be operable to control the flows of the first and second gas through the first and second gas inlet channels in dependence of each other so as to obtain a desired gas mixture as said carrier gas.

Thus, according to this aspect of the invention, not only does the vaporizer arrangement serve as a combined vaporizer and storage tank, it also serves as a gas mixing chamber. By letting the mixing of gas components forming the carrier gas, and the vaporization of liquid into the carrier gas, take place within the same space, i.e. within the vaporization chamber, the number of components in the gas flow circuit, and hence the complexity and cost of the gas flow circuit, can be reduced.

To allow mixing of more gas components, the vaporization chamber may comprise yet further gas inlets. For example, the vaporization chamber may comprise three gas inlets for introduction of air, oxygen and nitrous oxide, respectively, into the vaporization chamber.

In embodiments where the vaporizer arrangement has a number of gas inlet channels for a respective carrier gas component, the flow of the respective carrier gas component into the vaporization chamber is preferably, in addition to the pressure in the vaporization chamber, controlled based on gas composition measurements and/or settings, so as to obtain a desired carrier gas mixture within the vaporization chamber and hence a desired gas mixture for delivery to the patient. The gas composition measurements can be obtained by means of a gas analyzer arranged within the vaporization chamber or the gas outlet channel, and/or by a gas analyzer arranged in closer proximity to the patient, for example in a Y-piece of the breathing apparatus.

Preferably, where the vaporizer arrangement has a plurality of gas inlet channels, the flow regulating means has a controllable valve in each of the respective gas inlet channels.

To achieve efficient mixing of any carrier gas components and the vapor component within the vaporization chamber, the gas inlet channel(s) and the gas outlet channel may be arranged in relation to each other so as to create a high degree of turbulence within the vaporization chamber. Instead or in addition to a certain arrangement of the gas inlet and outlet channels, the vaporizer arrangement may comprise turbulence generating means arranged to further increase the turbulence within the vaporization chamber. The turbulence generating means may comprise a fan for generating a forced flow within the vaporization chamber, and/or flow benders for redirecting the natural flow of carrier gas or carrier gas components entering the vaporization chamber through the gas inlet channel(s).

The vaporizer arrangement may be designed as an injection vaporizer. In this case, the vaporization means for vaporization of the liquid into the carrier gas may comprise an injection nozzle for injecting fine droplets of liquid into the carrier gas in the vaporization chamber and a liquid flow control valve for controlling the flow of liquid through the injection nozzle.

The vaporizer arrangement may also be designed as a flow-by vaporizer. In this case, the vaporization means may comprise nothing but a receptacle for holding a volume of liquid to be vaporized into the carrier gas. The receptacle may be a lower portion of the vaporization chamber.

The present invention also concerns a breathing apparatus comprising a vaporizer arrangement as described above. The breathing apparatus may be an anaesthesia apparatus wherein the vaporizer arrangement is an anaesthetic vaporizer for adding anaesthetic agent to a breathing gas. The breathing apparatus may also be a conventional ventilator or any other device for providing respiratory support to a patient, wherein the vaporizer arrangement is a humidifier for humidifying a breathing gas through vaporization of water.

BRIEF DESCRIPTION OF THE DRAWINGS

FIG. 1 illustrates an embodiment of a breathing apparatus according to the invention.

FIG. 2 illustrates an embodiment of a vaporizer arrangement according to the invention.

FIGS. 3 and 4 illustrate other embodiments of a breathing apparatus according to the invention.

FIGS. 5 and 6 illustrate other embodiments of a vaporizer arrangement according to the invention.

FIG. 7 illustrates an embodiment of a gas tank arrangement according to one aspect of the invention.

FIGS. 8 and 9 illustrate embodiments of a gas tank arrangement according to another aspect of the invention.

DESCRIPTION OF THE PREFERRED EMBODIMENTS

Vaporizer Arrangement for Apparatus

FIG. 1 illustrates an example of a breathing apparatus 1A according to one embodiment of the invention.

In this embodiment, the breathing apparatus 1A is an anaesthesia apparatus for delivery of inhalation anaesthetic to a patient 2 during respiratory treatment. The anaesthesia apparatus has a drive unit 3, which may comprise a ventilator, for the supply and regulation of breathing gases. It further has a breathing circuit which, in this embodiment, is a circle system comprising an inspiratory branch 4 and an expiratory branch 5. Gases exhaled by the patient 2 are conveyed through the expiratory branch 5 and resupplied to the patient 2 via the inspiratory branch 4 after removal of carbon dioxide by means of a carbon dioxide absorber 6 in the inspiratory branch. Furthermore, the apparatus 1 has a vaporizer arrangement 7A for supply of an anaesthetic agent to the patient 2 via a fresh gas supply line 8.

FIG. 2 illustrates the vaporizer arrangement 7A of FIG. 1 in greater detail. With reference simultaneously made to FIG. 1, the vaporizer arrangement 7A is seen to comprise a vaporization chamber 9 in which liquid anaesthetic is vaporized into a carrier gas for subsequent delivery to the patient 2 via the fresh gas supply line 8. The carrier gas is supplied to the vaporization chamber 9 via a gas inlet channel 10. The carrier gas may be constituted by a single gas component but is typically a mixture of a plurality of carrier gas components, such as air, oxygen and nitrous oxide. The carrier gas is delivered to the vaporizer arrangement 7A from the drive unit 3 at an overpressure. To this end, the drive unit 3 may be connected to one or more medical gas wall outlets delivering pressurized medical gases or it may comprise one or more compressors for pressuring the carrier gas. In other embodiments, the vaporizer arrangement itself 7A may comprise means for pressurizing the carrier gas, such as one or more compressors.

The vaporizer arrangement 7A is further seen to comprise a liquid inlet 11 for introducing liquid anaesthetic into the vaporization chamber 9. In this embodiment, the vaporizer arrangement is an injection vaporizer comprising liquid injection means for actively injecting the anaesthetic liquid into the carrier gas. The liquid injection means has an injection nozzle 12A and a liquid flow control valve 12B for controlling the flow of liquid anaesthetic through the nozzle 12A and into the vaporization chamber 9.

The vaporizer arrangement 7A may further comprise heating means 14 for heating the vaporization chamber 9 to a temperature at which a desired degree of vaporization of the liquid is achieved.

To achieve efficient mixing of the carrier gas components and the vapor component within the vaporization chamber 9, the vaporizer arrangement may comprise turbulence generating means 15 for increasing the turbulence within the vaporization chamber. Here, the turbulence generating means 15 are gas flow benders in form of elements protruding from the inner wall of the vaporization chamber 9 and at least partly into the flow paths of the carrier gas delivered through the gas inlet channel 10. A net arranged near the opening of the gas inlet channel 10 in the vaporization chamber 9 may also be used as turbulence generating means. Other types of turbulence generating means, such as one or more fans for generating a forced flow of gas in the vaporization chamber 9, may also be used to increase the turbulence. The turbulence generating means 15 serves to obtain a more homogeneous mixture of the carrier gas and the vapor component in the vaporization chamber.

Furthermore, the vaporizer arrangement 7A has a gas outlet channel 18 for delivery of the vapor-containing gas from the vaporization chamber 8 to the patient 2, i.e. for delivery of the carrier gas after absorption of vaporized liquid. In this embodiment, the gas outlet channel 18 is connected to the fresh gas delivery line 8.

The vaporizer arrangement may further comprise a gas analyzer 19 for determination of the gas composition of the vapor-containing gas. The gas analyzer may be configured to determine the concentration of the vapor component in the carrier gas, but also the concentrations of various gas components in the carrier gas. In this embodiment, the gas analyzer 19 is arranged in the gas outlet channel 18. However, the gas analyzer may also be arranged within the vaporization chamber 9.

The vaporizer arrangement has gas flow regulating means for maintaining the carrier gas within the vaporization chamber 8 at an overpressure, and to control the flow of vapor-containing gas out of the vaporization chamber in a variable manner. This means that the gas flow regulating means is configured to vary said flow based on measured parameters and/or parameter settings set by an operator of the breathing apparatus 1A.

To this end, the gas flow regulating means may comprise a controllable outlet valve 17 which is regulated by a control unit (not shown) of the vaporizer arrangement 7A or the breathing apparatus 1A based on measured parameters, and typically also based on preset parameters set by an operator of the breathing apparatus 1.

The vaporizer arrangement 7A further has pressure monitoring means for monitoring the pressure in the vaporization chamber 9. The pressure monitoring means may comprise a pressure sensor 21 arranged to measure the pressure in the vaporization chamber 9, and/or flow sensors 22, 23A-B arranged to measure the flows in and out of the vaporization chamber, which flows are indicative of the pressure within the vaporization chamber 9. The pressure monitoring means are coupled to the control unit to allow the gas flow regulating means to be controlled based on the measured pressure and/or flows.

Furthermore, the vaporization chamber is seen to comprise a flush outlet 24 for flushing gas and/or liquid out of said vaporization chamber 9. The gas flow regulating means of the vaporizer arrangement is configured to control the flow of gas out of the vaporization chamber through said flush outlet 24. To this end, the gas flow regulating means may comprise a flush valve 25, also controlled by the control unit of the vaporizer arrangement or the breathing apparatus based on measured and/or preset parameters.

In a basic embodiment of the invention, a flow of pressurized gas is received through the gas inlet channel 10 from one or more gas sources (not shown). The controllable outlet valve 17 is configured to maintain the gas within the vaporization chamber at an overpressure, relative to the pressure in the gas outlet channel 18, and to control the flow through the gas outlet channel 18 in a variable manner. To avoid too high pressure build-up in the vaporization chamber 9, the flush valve 25 may be configured to flush excess gas out of the vaporization chamber 9 when the pressure therein exceeds a maximum threshold value.

In the above described embodiment, it is not required to control the flow of carrier gas into the vaporization chamber 9 through the gas inlet channel 10.

In a preferred embodiment of the invention, however, the gas flow regulating means of the vaporizer arrangement 7A further has a controllable inlet valve 26 which is also controlled by the control unit of the vaporizer arrangement or the breathing apparatus 1A based on measured and/or preset parameters.

The outlet valve 17 and the inlet valve 26 may be configured to cooperatively control the gas flow into and out of the vaporization chamber 9 so as to maintain the gas therein at the desired overpressure.

In one embodiment, the inlet valve 26 is controlled based on the pressure in the vaporization chamber 9, while the outlet valve 17 is controlled based on pressure and/or flow measurements obtained downstream of the vaporization chamber 9 and indicative of the respiratory phase of the patient 2. Preferably, the outlet valve 17 is controlled to deliver a varying flow of gas from the vaporization chamber 9, which flow is adapted to the respiration cycle of the patient 2, and the inlet valve 26 is controlled so as to maintain the pressure in the vaporization chamber 9 between a minimum pressure threshold value and a maximum pressure threshold value.

The minimum pressure threshold value is selected such that a sufficient flow of gas can be delivered from the vaporization chamber 9 during inspiration phases of the patient 2. To this end, the minimum pressure threshold value is preferably selected such that the desired flow profile can be delivered to the patient via the outlet valve 17 during inspiration of the patient 2. In order to maintain the pressure in the vaporization chamber 9 above said minimum pressure threshold value throughout the inspiration phases of the patient, the flow regulating means 17, 25, 26 controls the inflow and outflow into and out of the vaporization chamber 9 to obtain a pressure corresponding to the maximum pressure threshold value in the vaporization chamber 9 during expiration of the patient. The maximum pressure threshold value should be reached at least at the end of each expiratory phase, and so corresponds to an end-expiratory target pressure in the vaporization chamber. This maximum pressure/end-expiratory target pressure is selected such that too high flows of gas to the patient 2 is avoided even if the outlet valve 17 should go from a closed position to a fully open position at said pressure. However, it should be selected high enough to ensure that a sufficiently high flow and volume of vapor-containing gas can be delivered to the patient 2 during the following inspiration. The maximum pressure threshold value and the dynamics of the outlet valve 17 set an upper limit for the flow of vapor-containing gas that can be delivered to the patient 2.

During expiration phases of the patient, the outlet valve 17 is preferably controlled to fully quench the flow of vapor-containing gas out of the vaporization chamber 9, while the inlet valve 26 is controlled to obtain the end-expiratory target pressure in the vaporization chamber. The outlet valve 17 may also be controlled such that a low bias flow of vapor-containing gas is delivered to the patient 2 from the vaporization chamber 9 during expiration phases. During inspiration phases of the patient 2, the outlet valve 17 is opened and regulated such that the overpressure in the vaporization chamber 9 causes a desired flow of vapor-containing gas to leave the vaporization chamber through the gas outlet channel 18. The inlet valve 26 may be closed during inspiration of the patient 2. In some embodiments, however, the inlet valve 26 may be open during the whole or parts of the inspiration phase, and regulated so as to maintain the pressure in the vaporization chamber 9 above the minimum pressure threshold value.

In some embodiments, the inlet valve 26 and the outlet valve 17 of the vaporizer arrangement 7A may hence be controlled such that they are never open simultaneously, in order for the vaporization chamber 9 to serve as a gas lock wherein the gas is maintained at an overpressure between the minimum and maximum pressure threshold values.

The outlet valve 17 may be controlled to deliver a constant flow of vapor-containing gas during the inspiration phase of the patient, or it may be controlled to deliver a flow that varies during the inspiration phase based on measured and/or preset parameters.

The capability of delivering a controlled and varied flow during inspiration phases is advantageous in that the flow of vapor-containing gas from the vaporization chamber 9 can be adjusted to deliver a preset tidal volume to the patient 2, or to maintain a preset proximal pressure in the breathing circuit, substantially corresponding to the airway pressure of the patient 2. Compared to a conventional fresh gas vaporizer which is a passive component through which the carrier gas passes freely, this makes the vaporizer arrangement 7A an active, flow regulating component that can take over some or all of the functionality normally provided for by the drive unit 3 of the breathing apparatus.

Figure 3:
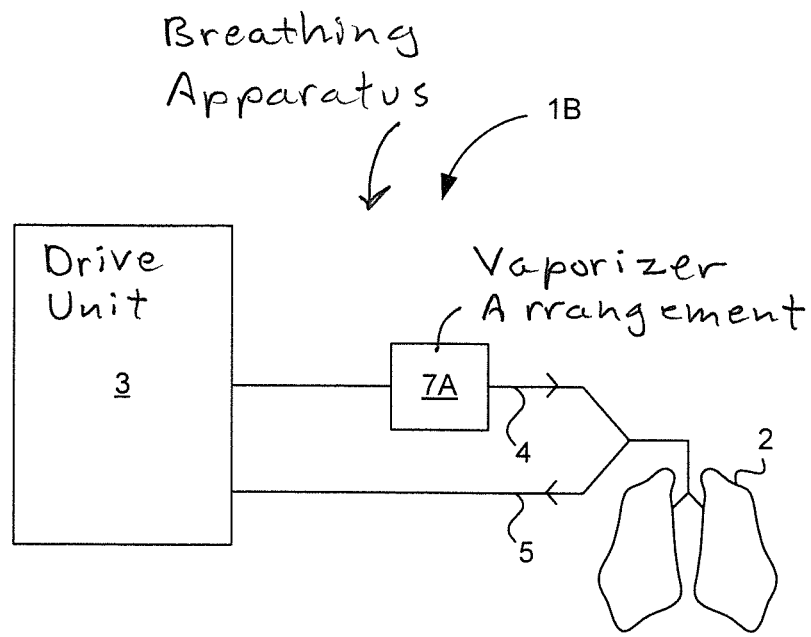

FIG. 3 illustrates an example of a breathing apparatus 1B according to another embodiment of the invention.

In contrast to the vaporizer arrangement of the breathing apparatus 1A in FIG. 1, the vaporizer arrangement 7A is here intended and configured to deliver the entire tidal volume of breathing gas to the patient 2 during inspiration.

Figure 2:
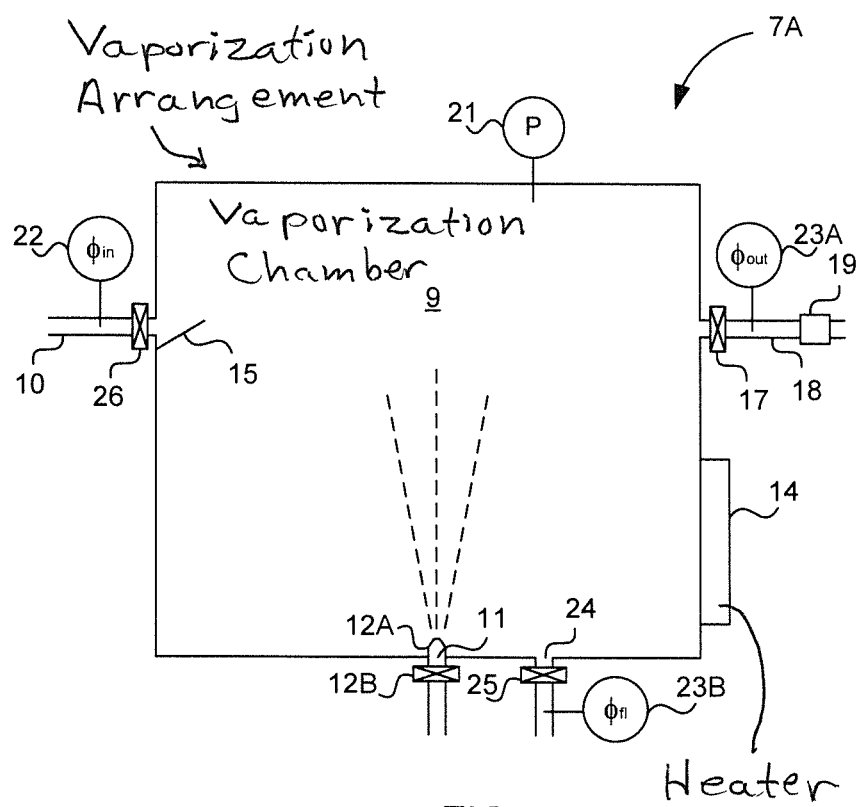

With simultaneous reference now made to FIGS. 2 and 3, this means that the volume of the vaporization chamber 9 and the overpressure at which the gas is maintained in the vaporization chamber 9 preferably are selected such that the vaporizer arrangement 7A is capable of delivering at least 600 ml of vapor-containing gas during an inspiration phase of the patient 2, substantially corresponding to a tidal volume of an adult patient with normal lung capacity. Also, the gas flow regulation means is configured to deliver vapor-containing gas from the vaporization chamber 9 at a flow that is maintained over 120 lpm during the entire inspiration phase of the patient 2.

The volume of the vaporization chamber 9 and the overpressure at which the gas is maintained in the vaporization chamber are important design parameters in order to deliver the desired flow and volume of vapor-containing gas from the vaporization chamber 9 during an inspiration phase. A vaporization chamber volume of 500 ml is sufficient to deliver 1000 ml of vapor-containing gas during an inspiration phase without the need for opening the inlet valve 26 to refill the vaporization chamber 9 with carrier gas during said inspiration phase, if the pressure in the vaporization chamber is 4 bar at the end of expiration (i.e. at start of inspiration) and 2 bar at the end of inspiration. If the pressure in the vaporization chamber 9 goes from 2 bar to 1 bar during inspiration, the volume of the vaporization chamber should be at least 1000 ml to deliver the same volume of gas, and if it goes from 1 bar to 0.5 bar, the volume of the vaporization chamber 9 should be at least 2000 ml. Also, the dynamics of the outlet valve 17 should be adapted to the pressure range of the vaporization chamber in order to deliver the desired flow of vapor-containing gas to the patient 2.

Figure 4:
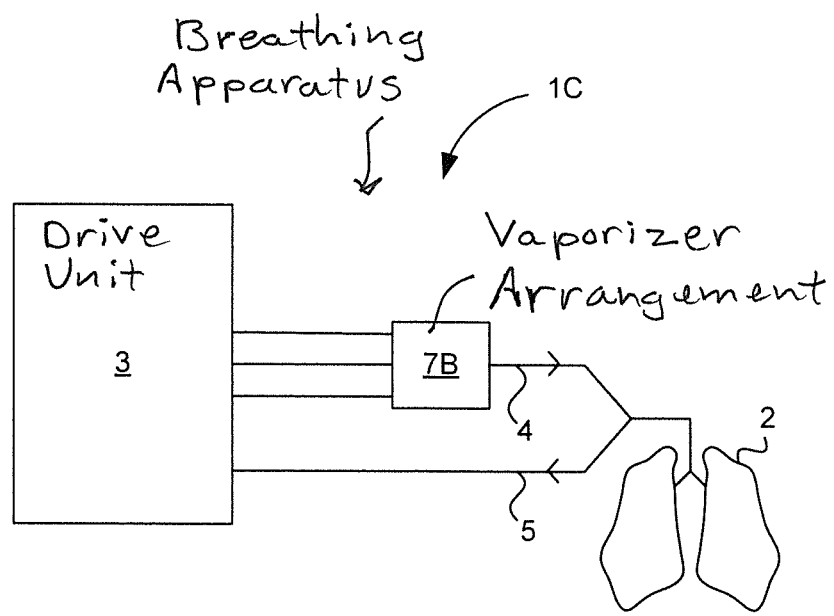

FIG. 4 illustrates an example of a breathing apparatus 1C according to yet another embodiment of the invention. Just like the breathing apparatus 1B in FIG. 3, the breathing apparatus 1C has a vaporizer arrangement 7B configured to deliver the entire tidal of breathing gas to the patient 2. In this embodiment, however, not only does the vaporizer arrangement 7B serve as a combined vaporizer and pressurized supply of vapor-containing gas for direct delivery to the patient 2, it also serves as a gas mixing chamber.

Figure 5:
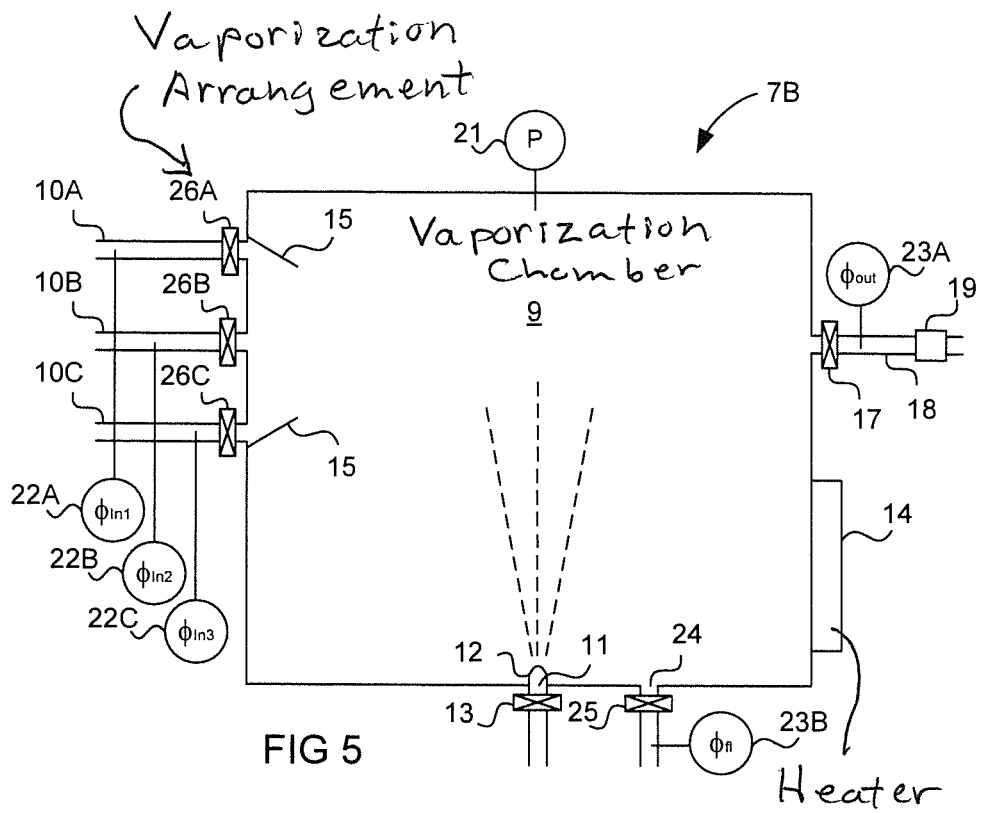

With simultaneous reference now made to FIG. 5 which shows the vaporizer arrangement 7B in greater detail, the breathing apparatus 1C is configured to deliver different pressurized carrier-gas components to a plurality of gas inlet channels 10A-10C of the vaporizer arrangement 7B. The carrier-gas components are preferably two or more in the group consisting of air, oxygen and nitrous oxide.

The gas flow regulating means of the vaporizer arrangement 7B has a controllable inlet valve 26A-C in the respective gas inlet channel 10A-10C, each controlled by a control unit of the vaporizer arrangement 7B or the breathing apparatus 10 based on measured and/or preset parameters. The controllable inlet valves 26A-C and the outlet valve 17 cooperatively control the gas flow into and out of the vaporization chamber 9 so as to maintain the gas therein at the desired overpressure.

Also, the inlet valves 26A-C are controlled in dependence of each other so as to obtain a desired carrier gas mixture within the vaporization chamber 9. To this end, the inlet valves 26A-C may be controlled based on both the pressure within the vaporization chamber 9 and the composition of the gas within the vaporization chamber or downstream of the vaporization chamber 9, which may be measured by means of the gas analyzer 19.

It should be appreciated that the inlet valves 26A-C and the outlet valve 17 are configured to cooperatively control the flow of gas into and out of the vaporization chamber in the way described above with reference to the single inlet valve and the outlet valve of the vaporizer arrangement 7A in FIG. 2. Likewise, the discussion on the volume of the vaporization chamber 9, the minimum and maximum pressure threshold values etc. also applies to the vaporizer arrangement 7C of this embodiment.

Figure 6:
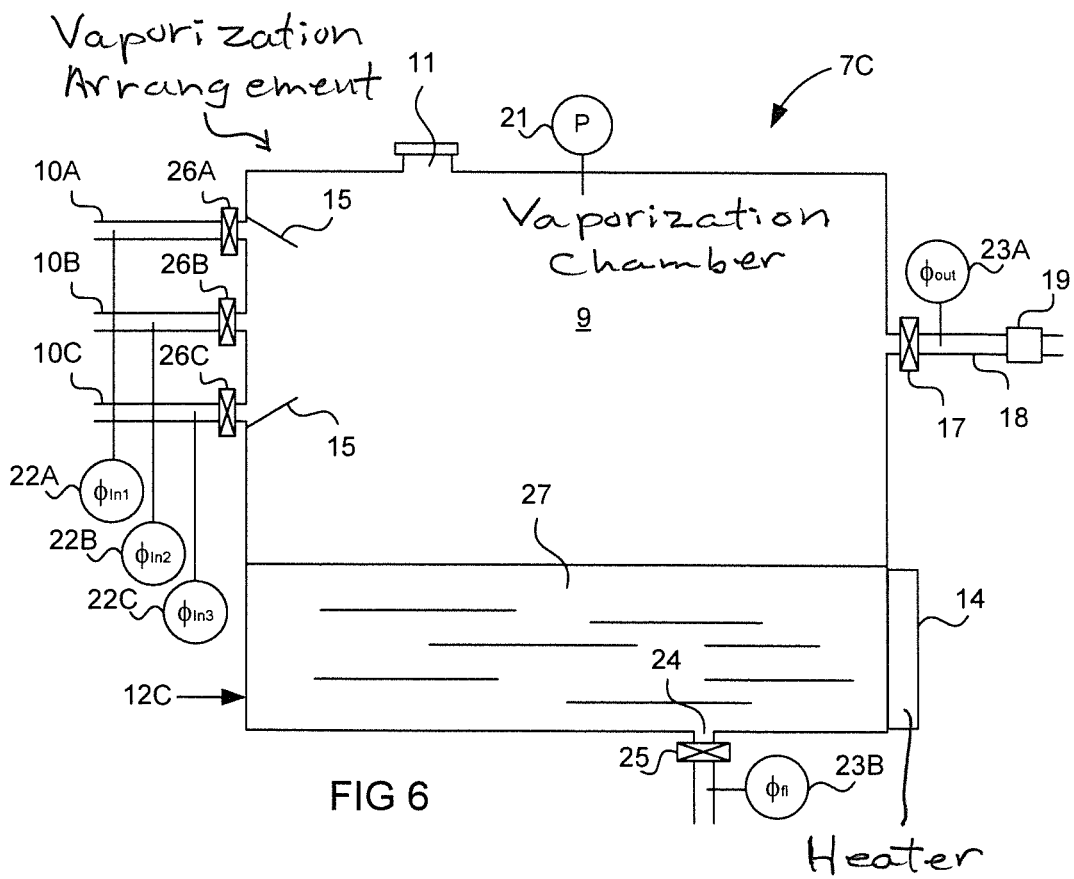

FIG. 6 illustrates yet another embodiment of a vaporizer arrangement 7C according to the invention. In contrast to the previously described vaporizer arrangements 7A, 7B being injection vaporizers, the vaporizer arrangement 7C is a flow-by vaporizer for vaporization of a liquid 27. The vaporizer arrangement 7C may be an anaesthetic vaporizer in which case the liquid 27 is liquid anaesthetic or a humidifier in which case the liquid is water.

The major difference between this vaporizer arrangement 7C and the vaporizer arrangement 7B in FIG. 5 is that this vaporizer arrangement 7C has a receptacle 12C for the liquid 27 to be vaporized instead of an injection arrangement. The temperature of the liquid 27 is controlled through the supply of heat by means of the heat generating means 14 such that the liquid passively vaporizes into the gas that is maintained in the vaporization chamber 9. In this embodiment, the liquid receptacle 12B is formed by a lower portion of the vaporization chamber 9, arranged to receive and retain liquid. Furthermore, the liquid inlet 11 of the vaporizer arrangement is arranged in an upper portion of the vaporization chamber 9 such that the receptacle 12C can be refilled via the liquid inlet.

Besides the above differences, it should be appreciated that the vaporizer arrangement 7C is arranged as the vaporizer arrangement 7B described above with reference to FIG. 5.

Flow Control in Pressurized Gas Tank

While the above description relates to a new type of vaporizer arrangement where vaporization takes place in a pressurized gas tank, the following description relates to pressurized gas tanks in general.

Pressurized gas tanks are often used in breathing apparatuses for mixing and/or storage of breathing gases that are to be delivered to a patient. An example of a breathing apparatus comprising such a gas tank is disclosed in U.S. Pat. No. 5,299,568.

In gas tank arrangements according to prior art, the outlet valve controlling the flow of gas out of the tank and towards the patient function as a conventional inspiration valve and is controlled based on pressure and/or flow measurements obtained downstream of the outlet valve, and preset ventilation parameters set by the operator of the breathing apparatus.

To avoid too high flows and pressures of gas from the gas tank to the patient, breathing apparatuses with pressurized gas tanks normally has a safety relief valve downstream of the outlet valve of the gas tank for venting breathing gas out of the system in case of too high pressure in the breathing circuit. The safety relief valve is controlled based on pressure measurements obtained downstream the outlet valve of the gas tank.

To avoid the situation where breathing gas must be vented out of the system through a safety relief valve, it is suggested, according to one aspect of the present invention, that the outlet valve that controls the flow of gas out of the gas tank is controlled based on the pressure within the gas tank.

Figure 7:
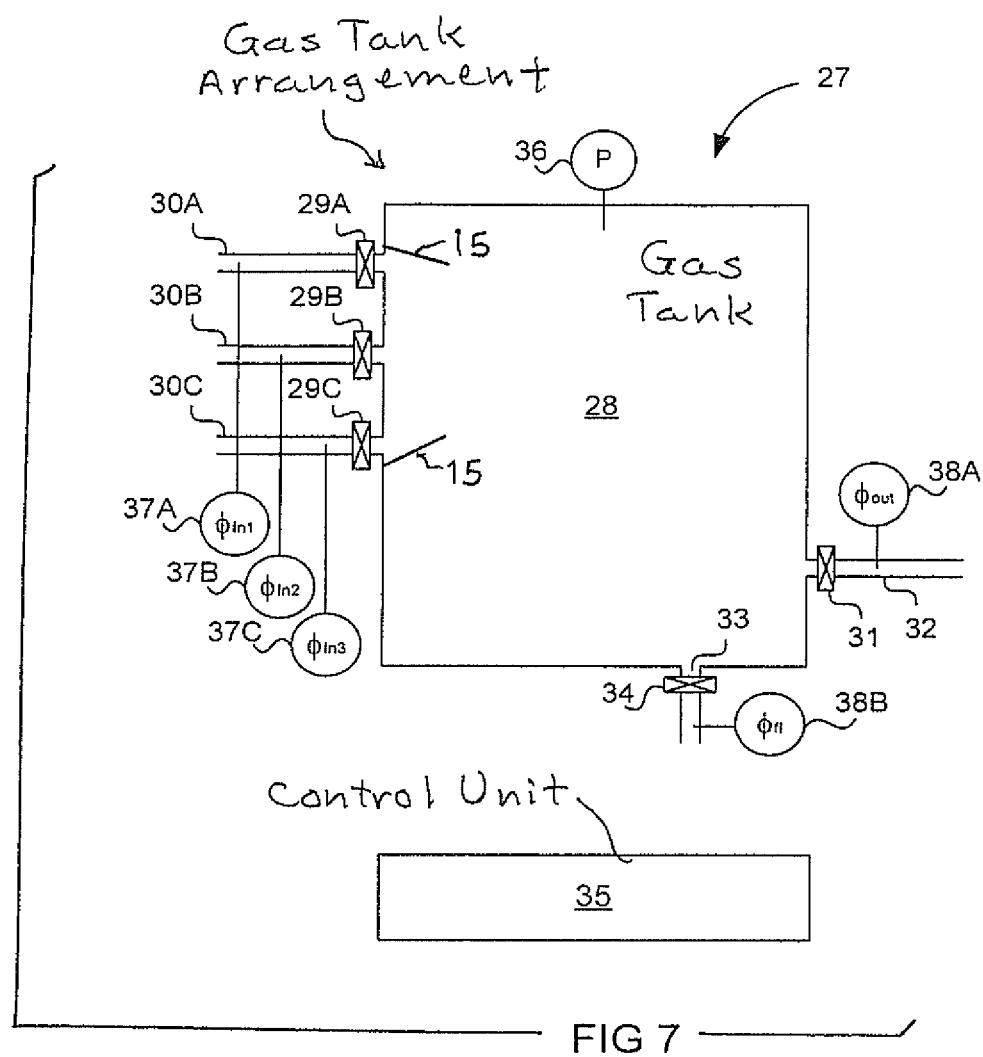

FIG. 7 illustrates a gas tank arrangement 27 according to this aspect of the invention. The gas tank arrangement 27 has a gas tank 28, at least one inlet valve 29A-C for controlling a flow of gas into said gas tank via at least one gas inlet channel 30A-C, and an outlet valve 31 for controlling the flow of gas out of the gas tank 28 and towards a patient via a gas outlet channel 32.

It should be appreciated that the gas tank arrangement 27 is intended to be used in a breathing apparatus, such as the breathing apparatus 1C in FIG. 4, in which it may replace the vaporizer arrangement 7B.

Preferably, the gas tank 28 serves as a mixing chamber in which two or more gas components such as air, oxygen and nitrous oxide, are mixed to form a breathing gas that is to be delivered to a patient. To this end, the gas tank arrangement 27 may comprise two or more inlet valves 29A-C for controlling the flow of two or more gas components into the gas tank 28. It should, however, be appreciated that the gas components could also be mixed upstream of the gas tank arrangement 27 and that the gas mixture could be delivered to the mixing chamber through a single inlet channel 30A under the control of a single inlet valve 29A of the gas tank arrangement.

The gas tank arrangement 27 may further comprise a flush outlet 33 for flushing gas out of the gas tank 28 via a flush outlet channel, and a flush valve 34 for controlling the flow of gas out of the gas tank 28 through said flush outlet 33.

The gas tank arrangement further has a control unit 35 which is configured to control the at least one inlet valve 29A-C and the outlet valve 31 to maintain the gas within the gas tank 28 at an overpressure for subsequent delivery to the patient. The control unit 35 is configured to control the at least one inlet valve 29A-C and the outlet valve 31 of the gas tank arrangement 27 such that they cooperatively control the flow of gas into and out of the gas tank 28 in the way the at least one inlet valve 26, 26A-26C and the outlet valve 17 control the flow of gas into and out of the vaporization chamber 9 of the vaporizer arrangements 7A-7C, described above with reference to FIGS. 1 to 6.

It should be appreciated that the discussion on the volume of the vaporization chamber 9 and the minimum and maximum threshold values for the overpressure within the vaporization chamber 9, discussed above with reference to FIG. 2, also applies to the volume of the gas tank 28 and the regulation of the overpressure therein.

Besides being configured to control the at least one inlet valve 29A-C and the outlet valve 31 as previously described, the control unit 35 is further configured to control the outlet valve 31, and hence the flow of gas out of the gas tank 28, based on the pressure within the gas tank.

That the outlet valve 31 is controlled based on the pressure within the gas tank 28 means that the gas tank pressure is used by the control unit 35 as a variable in the control function for controlling the outlet valve 31. The pressure in the gas tank may be obtained directly from a pressure sensor 36 in the gas tank, or it may be calculated from other measured parameters, such as the flow of gas into and out of the gas tank, measured by flow sensors 37A-C, 38A in the gas inlet channel(s) 30A-C and the gas outlet channel 32, and additionally also a flow sensor 38B arranged in a flush outlet channel.

Controlling the outlet valve 31 based on the pressure in the gas tank 28 has the effect of being able to prevent too high flows from ever being delivered from the gas tank since the flow through the valve can be predicted by the control unit 35 given the pressure in the gas tank 28 and the dynamics of the outlet valve 31.

This eliminates the risk of delivering too high flows of breathing gas from the gas tank 28 towards the patient, and thus eliminates the need for venting breathing gas out of the breathing apparatus downstream of the gas tank arrangement 27.

It further has the effect of allowing the function of the outlet valve 31 to be adapted to the current gas tank pressure.

This in turn allows relatively high flows to be delivered from the gas tank 28 even at low gas tank pressures since the dynamics of the outlet valve can be adapted to allow a higher degree of opening of the valve at low pressures than at high pressures.

In one embodiment, the control unit 35 is adapted to determine an allowable range of operation of the outlet valve 31 based on the gas tank pressure, and to control the outlet valve 31 to operate only within said allowable range. The range of operation here means the degree of opening of the outlet valve 31. To this end, the control unit 35 may be configured to determine a maximum degree of opening of the outlet valve 31 which, under the prevailing pressure condition in the gas tank 28, corresponds to a certain maximum flow of gas out of the gas tank, and to control the outlet valve 31 such that it is never opened to a higher degree than said maximum degree of opening.

Preferably, the control unit 35 is adapted to determine the allowable range of operation based on the gas tank pressure and a parameter that is indicative of the lung capacity of the patient, such as a preset tidal volume of the patient, a preset minute ventilation of the patient, or a preset parameter indicating whether the patient is an adult or a child. This allows the maximum flow of gas out of the gas tank 28 to be tailored to the currently ventilated patient.

Even more preferably, the allowable range of operation of the outlet valve 31 is adaptive and the control unit configured to adapt it based on changes in the gas tank pressure. For example, the control unit 35 may be configured to determine a first maximum degree of opening of the outlet valve which should apply to pressures within a first pressure range, and a second maximum degree of opening of the outlet valve 31 which should apply to pressures within a second pressure range. In this way, the maximum degree of opening of the outlet valve can be high at low pressures and low at high pressures, which ensures that a sufficient flow of gas can be delivered at low pressures and that too high flows are avoided at high pressures. From a safety point of view it is advantageous to decrease the maximum degree of opening of the outlet valve if an increase is gas tank pressure is detected.

Using a slightly different wording, the control unit 35 can, in this embodiment, be said to adapt the resolution of the outlet valve 31 to the pressure in the gas tank 28, such that flows within a desired range of flows can be delivered to the patient, even if the pressure in the gas tank 28 varies substantially. The desired range of flows may be determined based on the previously mentioned parameter that is indicative of the lung capacity of the patient.

The outlet valve 31 is preferably electronically controlled. In one embodiment the outlet valve is an electronically controlled solenoid valve. In this case the degree of opening of the solenoid valve depends on the magnitude of an applied control current, and the control unit 35 may be configured to determine a maximum value for the control current so as to set a maximum degree of opening of the outlet valve.

The above described feature of controlling the outlet valve 31 based on the pressure within the gas tank 28 is applicable also to the previously described vaporizer arrangements 7A-7C. Thus, it should be understood that the outlet valve 17 in FIGS. 2, 5 and 6 also may be controlled based on the pressure within the vaporization chamber 9.

Efficient Flushing of Gas Tank

When using pressurized gas tanks as described above, there is sometimes a need for flushing the gas out of the gas tank as quickly as possible. This may for example be the case when there is an urgent need to change from one breathing gas composition to another.

Therefore, most gas tank-equipped breathing apparatuses comprise a flush valve for flushing the gas out of the gas tank and into open air or a scavenging system. This is typically achieved by closing the outlet valve of the gas tank arrangement and opening the flush valve while supplying a flow of flushing gas into the gas tank via the gas inlet channel. After a while, the flushing gas has replaced the previous gas in the gas tank. If flushing of the gas tank is made due to a desire to switch to another breathing gas composition, the "other" breathing gas composition is typically used as flushing gas.

However, the flushing procedure often takes too long time. Typically, a very large volume of flushing gas is required to flush a relatively small volume of gas out of the gas tank. How much flushing gas is required to flush a sufficiently large portion of the previous gas out of the gas tank depends on the flow of the flushing gas and, in particular, on the design of the gas tank.

A gas tank arrangement that solves or at least mitigates this problem will now be described with reference to FIGS. 8 and 9.

Figure 8:
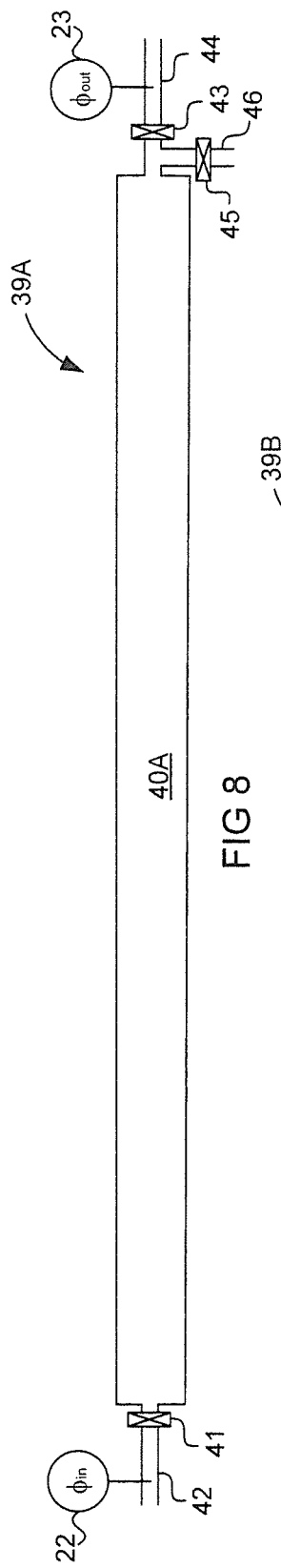

FIG. 8 illustrates a gas tank arrangement 39A for a breathing apparatus, comprising a gas tank 40A, at least one inlet valve 41 for controlling a flow of gas into said gas tank 40A via a gas inlet channel 42, an outlet valve 43 for controlling the flow of gas out of said tank 40 and towards a patient via a gas outlet channel 44, and a flush valve 45 for enabling flushing of gas out of the gas tank 40A via a flush outlet channel 46.

Preferably, the gas tank 40A serves as a mixing chamber in which two or more gas components, such as air, oxygen and nitrous oxide, are mixed. To this end, the gas tank 40A may comprise two or more inlet valves for controlling the flow of two or more gas components into the gas tank 40A via two or more gas inlet channels, in accordance with the embodiment of the gas tank arrangement 27 illustrated in FIG. 7. In this embodiment, however, the gas tank arrangement 39A is seen to comprise a single inlet valve 41 and the gas components that form the breathing gas are premixed in a mixing stage (not shown) upstream of the inlet valve 41 for further mixing in the mixing chamber constituted by the gas tank 40A.

It should be appreciated that the gas tank arrangement 39A is intended to be used in a breathing apparatus, such as the breathing apparatus 1C in FIG. 4, in which it may replace the vaporizer arrangement 7B.

The at least one inlet valve 41 and the outlet valve 43 are configured to maintain the gas within the gas tank 40A at an overpressure for subsequent delivery to the patient. To this end, the at least one inlet valve 41 and the outlet valve 43 cooperatively control the flow of gas into and out of the gas tank 40A in the way the at least one inlet valve 26, 26A-26C and the outlet valve 17 control the flow of gas into and out of the vaporization chamber 9 of the vaporizer arrangements 7A-7C, described above with reference to FIGS. 1 to 6.

It should be appreciated that the discussion on the volume of the vaporization chamber 9 and the minimum and maximum threshold values for the overpressure within the vaporization chamber 9, discussed above with reference to FIG. 2, also applies to the volume of the gas tank 40A and the regulation of the overpressure therein.

As illustrated in the drawing, the gas tank 40A is elongated and at least one of the at least one inlet valves 41 and the outlet valve 43 are arranged in opposite ends of the elongated gas tank 40A. The flush valve 45 is arranged in the same end as the outlet valve 43 so that gas can be efficiently pushed out of the gas tank 40A through the flush valve 45 by a flow of gas through the inlet valve 41 when the outlet valve 43 is closed. That the flush valve 45 is arranged in the same end as the outlet valve 43 means that it is arranged in the downstream-end of the elongated gas tank 40A.

For optimal flushing performance, the elongated gas tank 40A should be designed such that a well-defined front is formed between the gas that is to be flushed out of the gas tank 40A and the flushing gas that is supplied through the inlet valve 41, so that a minimum of mixing occurs between the gas volumes. In this way, the ratio between the volume of flushing gas needed to flush a gas out of the gas tank 40A, and the volume of the gas to be flushed out of the tank becomes nearly 1:1.

Preferably, to obtain the effect of efficient pushing of the gas out of the gas tank, the elongated gas tank 40A is configured such that a laminar flow is created in the longitudinal direction of the elongated gas tank when the flushing gas flows through the gas tank 40A towards the flush valve 45. In order for such a laminar flow to occur, the length of the elongated gas tank 40A should preferably be at least ten times the width of the gas tank (i.e. the diameter of the gas tank in case the tank has a circular cross-section).

Preferably, the maximum width of the tank is between 1 and 10 cm, and even more preferably between 3 and 7 cm. The elongated gas tank 40A is preferably a cylindrical gas tank in which case said maximum width corresponds to the diameter of the gas tank Even more preferably, the elongated gas tank 40A has a length of at least 60 cm and a width or diameter of at most 6 cm.

The gas tank 40A may further comprise local turbulence generating means (not shown) for generating a local turbulence in the gas tank. This is advantageous in that a laminar flow can be achieved in the gas tank even at a relatively short distance from the inlet of the gas tank (substantially shorter than 10 times the width of the gas tank), which further improves the effect of pushing the gas out of the gas tank. An additional effect of the local turbulence generating means is hence that the elongated gas tank 40A can be made shorter than 10 times its width while still allowing a laminar flow to occur in the tank. To obtain the laminar flow as close to the inlet of the gas tank 40A as possible, the local turbulence generating means is preferably arranged close to the inlet end of the elongated gas tank 40A, i.e. the end of the gas tank in which the inlet valve 41 is arranged.

Preferably, the local turbulence generating means is arranged to generate local turbulence along a direction that is substantially perpendicular to the longitudinal direction of the elongated gas tank. To this end, the local turbulence generating means may comprise one or more elements arranged in said plane. Preferably it has a plurality of elongated members arranged in said plane. In one embodiment, the local turbulence generating means has a net arranged in a plane that is substantially perpendicular to the longitudinal direction of the elongated gas tank. The net should preferably be arranged in the inlet end of the gas tank 40A.

Preferably, the volume of the elongated gas tank 40A is at least 500 ml, more preferably at least 1000 ml, and even more preferably at least 2000 ml.

The principle used to push the gas out of the gas tank is the same principle used in what is often referred to as a volume reflector, in which gases exhaled by the patient are collected in a hose and pushed back to the patient by a drive gas that is supplied through a distal end of the hose. Sometimes such volume reflectors are referred to as a Werner volumes after the inventor of U.S. Pat. No. 4,989,597 where the principle was first described.

The gas tank may be a straight tubular gas tank as illustrated in FIG. 8 but the demands on the volume and the cross section of the gas tank may, in view of other design requirements of the breathing apparatus of which it forms a part, require the elongated gas tank to be curved. Therefore, in some embodiments, the gas tank may be formed as a curved elongated gas flow channel. The volume of the gas flow channel should preferably be 1000 ml or more, and even more preferably 2000 ml or more.

Figure 9:
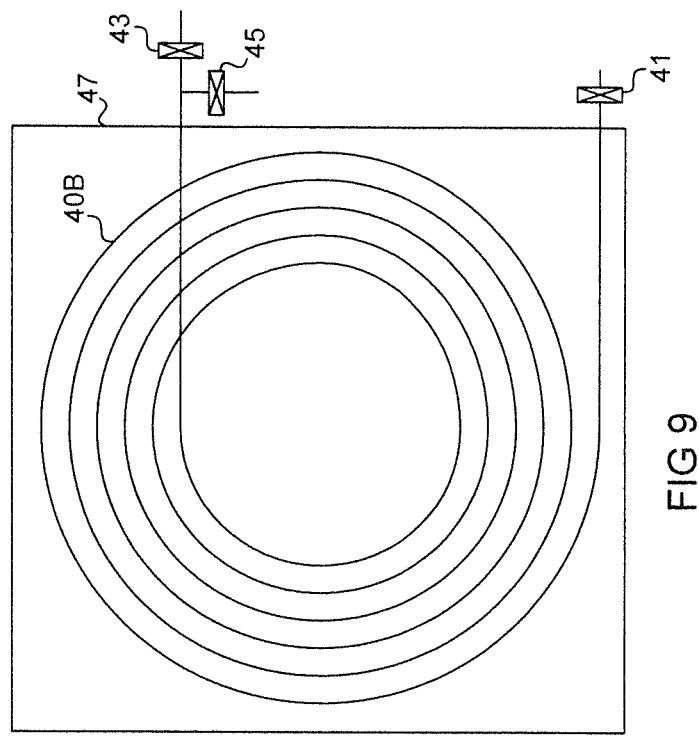

FIG. 9 illustrates an exemplary embodiment of a gas tank arrangement 39B comprising a gas tank 40B in form of a curved elongated gas channel. In this embodiment, the curved elongated gas channel forming the gas tank 40B is spiral-shaped and enclosed in a gas tank housing 47.

It should be appreciated that the vaporizer arrangement 7A, 7B, 7C described above with reference to FIGS. 1-6 also may be designed as described in this section in order to achieve the effect of more efficient flushing of vapor-containing carrier gas out of the vaporization chamber 9.

We claim as our invention:

1. A gas tank arrangement for a breathing apparatus, comprising:
   a gas tank;
   an inlet valve that controls a flow of gas into said gas tank;
   an outlet valve that controls the flow of gas out of said gas tank and toward a patient; and
   a control unit configured to control said inlet and outlet valves to maintain the gas within said gas tank at an overpressure for subsequent delivery to the patient;
   said control unit being configured to control the outlet valve based on at least one of pressure and flow measurements obtained downstream of said gas tank in order to deliver a varying flow of gas adapted to a respiration cycle of the patient situated downstream of said gas tank, and based on a parameter that is indicative of pressure within the gas tank, and to determine an allowable range of operation of said outlet valve based on said parameter, and to control the outlet valve to operate only within said allowable range.

2. A gas tank arrangement according to claim 1, wherein the control unit is configured to determine said allowable range of operation of the outlet valve based on said parameter and a second parameter indicative of the lung capacity of the patient.

3. A gas tank arrangement according to claim 1, wherein said allowable range of operation of the outlet valve is adaptive, and said control unit is configured to adapt the allowable range of operation of the outlet valve based on changes in the gas tank pressure.

4. A gas tank arrangement according to claim 3, wherein the control unit is configured to decrease the allowable range of operation of the outlet valve based on an increase in the gas tank pressure.

5. A gas tank arrangement according to claim 1, wherein the outlet valve is electronically controlled, and wherein a degree of opening of the outlet valve depends on a control current supplied to the outlet valve, and wherein the control unit is configured to determine said allowable range of operation of the outlet valve by determining a maximum value for said control current.

6. A gas tank arrangement according to claim 1, wherein said parameter indicative of pressure within the gas tank is obtained by a pressure sensor in the gas tank or by flow sensors arranged to measure the flow of gas into and out of the gas tank.

7. A gas tank arrangement according to claim 1, wherein the gas tank forms a mixing chamber for two or more gas components forming a breathing gas mixture that is to be supplied to the patient.

8. A gas tank arrangement according to claim 7, further comprising a gas mixing stage for mixing two or more gas components to be delivered to the gas tank, upstream of said inlet valve.

9. A gas tank arrangement according to claim 7, wherein said inlet valve controls the flow of a first gas component into the gas tank, and the gas tank arrangement further comprises a second inlet valve that controls a flow of a second gas component into the gas tank.

10. A gas tank arrangement for a breathing apparatus, comprising:
   a gas tank;
   an inlet valve that controls a flow of gas into said gas tank;
   an outlet valve that controls the flow of gas out of said gas tank, toward a patient; and
   a flush valve that enables flushing of gas out of said gas tank,
   said inlet and outlet valves being operable to maintain the gas within said tank at an overpressure for subsequent delivery to the patient; and
   the gas tank having a length that is at least ten times its width and an elongated tank shape with the inlet valve and the outlet valve situated at opposite ends of the elongated gas tank, and the flush valve situated in the same end as the outlet valve so that gas can be pushed out of the gas tank through the flush valve by a flow of gas supplied to the gas tank through the inlet valve, when the outlet valve is closed.

11. A gas tank arrangement according to claim 10, wherein the elongated gas tank comprises a local turbulence generator that generates local turbulence within the gas tank.

12. A gas tank arrangement according to claim 11, wherein said local turbulence generator comprises one or more elements in a plane that is perpendicular to a longitudinal direction of the elongated gas tank.

13. A gas tank arrangement according to claim 12, wherein said local turbulence generator is a net.

14. A gas tank arrangement according to claim 10, wherein the elongated gas tank has a maximum width or diameter between 1 and 10 cm.

15. A gas tank arrangement according to claim 10, wherein said gas tank forms an elongated gas flow channel between said inlet and said outlet, said gas flow channel being curved.

* * * * *